(12) United States Patent
Dahanukar et al.

(10) Patent No.: US 10,875,887 B2
(45) Date of Patent: Dec. 29, 2020

(54) PROCESS FOR PREPARATION OF OBETICHOLIC ACID

(71) Applicant: DR. REDDY'S LABORATORIES LIMITED, Hyderabad (IN)

(72) Inventors: Vilas Hareshwar Dahanukar, Hyderabad (IN); Rama Mohan Hindupur, Hyderabad (IN); Rashid Abdul Rehman Khan, Hyderabad (IN); Satishbhai Sukhlalbhai More, Hyderabad (IN); Vikas Sadashiv Gajare, Hyderabad (IN); Sandip Ramdas Khobare, Hyderabad (IN); Krishna Mohan Thalabathula, Hyderabad (IN); Rajender Datrika, Hyderabad (IN); Sreenivasulu Madi Shetty, Hyderabad (IN)

(73) Assignee: DR. REDDY'S LABORATORIES LIMITED., Hyderabad (IN)

( * ) Notice: Subject to any disclaimer, the term of this patent is extended or adjusted under 35 U.S.C. 154(b) by 211 days.

(21) Appl. No.: 16/304,821

(22) PCT Filed: May 31, 2017

(86) PCT No.: PCT/IB2017/053195
§ 371 (c)(1),
(2) Date: Nov. 27, 2018

(87) PCT Pub. No.: WO2017/208165
PCT Pub. Date: Dec. 7, 2017

(65) Prior Publication Data

US 2020/0317715 A1 Oct. 8, 2020

(30) Foreign Application Priority Data

Jun. 1, 2016 (IN) .............................. 201641018884

(51) Int. Cl.
*C07J 9/00* (2006.01)

(52) U.S. Cl.
CPC .................................... *C07J 9/005* (2013.01)

(58) Field of Classification Search
CPC ....................................................... C07J 9/005
See application file for complete search history.

(56) References Cited

U.S. PATENT DOCUMENTS

| 7,994,352 B2 | 8/2011 | Ferrari et al. |
| 10,407,462 B2 * | 9/2019 | Zampella ................ A61P 13/12 |

FOREIGN PATENT DOCUMENTS

| WO | 2002/072598 A1 | 9/2002 |
| WO | 2013/192097 A1 | 12/2013 |
| WO | 2015/181275 A1 | 12/2015 |

OTHER PUBLICATIONS

International Search Report dated Sep. 13, 2017, for corresponding International Patent Application No. PCT/IB2017/053195.
(Continued)

*Primary Examiner* — Paul A Zucker
(74) *Attorney, Agent, or Firm* — Pergament & Cepeda LLP; Milagros A. Cepeda; Edward D. Pergament

(57) ABSTRACT

The invention of the present application relates to the process for the preparation of intermediates of obeticholic acid and their conversion to obeticholic acid. The process involves the conversion of compound of formula (VI) to compound of formula (VII) in presence of an organic base.

10 Claims, 2 Drawing Sheets

(56) References Cited

OTHER PUBLICATIONS

Written Opinion dated Sep. 13, 2017, for corresponding International Patent Application No. PCT/IB2017/053195.
International Preliminary Report on Patentability dated Dec. 4, 2018, for corresponding International Patent Application No. PCT/IB2017/053195.
Hisatoshi Uehara et al.; "Organocatalytic asymmetric assembly reactions for the syntheses of carbohydrate derivatives by intermolecular Michael-Henry reactions", PNAS vol. 107 No. 48, Nov. 30, 2010.

* cited by examiner

PROCESS FOR PREPARATION OF OBETICHOLIC ACID

This application is a National Stage Application under 35 U.S.C. § 371 of PCT International Application No. PCT/IB2017/053195, filed May 31, 2017, which takes priority from Indian Provisional Application Numbers IN 201641018884, filed Jun. 1, 2016; all of which is herein incorporated in its entirety.

FIELD OF INVENTION

The present application relates to process for the preparation of intermediates of obeticholic acid and their conversion to obeticholic acid.

BACKGROUND

Obeticholic acid is a semi-synthetic bile acid analogue. It is an agonist of farnesoid X receptor (FXR) ligand. Obeticholic acid is indicated for the treatment of primary biliary cirrhosis (PBC). PCT patent application, WO2002072598A1 (hereinafter referred as the WO'598 application) discloses obeticholic acid and process for preparation thereof. Obeticholic acid is chemically known as 6α-ethyl-chenodeoxycholic acid and has following structural formula:

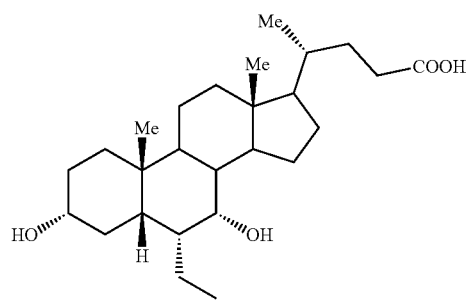 [SMILES: CC[C@H]1[C@@H](O)C2C3CCC([C@H](C)CCC(=O)O)[C@@]3(C)CCC2[C@@]2(C)CC[C@@H](O)C[C@@H]12]

U.S. Pat. No. 7,994,352B2 (hereinafter referred as the US'352 patent) discloses a process for the preparation of obeticholic acid. PCT patent application, WO2013192097A1 (hereinafter referred as the WO'097 application) discloses a process for preparing pure amorphous form of obeticholic acid comprising the step of converting crystalline form C of obeticholic acid to pure amorphous form.

Obeticholic acid is synthetic bile acid and hence achieving ICH grade of purity is known to be difficult. Moreover, the starting material for the synthesis of obeticholic acid is chenodeoxycholic acid which is obtained from animal origin. Hence, the purification of obeticholic acid is essential for the use of it as drug. Hence, there remains a need for an alternate commercially feasible process for the preparation of pure obeticholic acid which is suitable to be used as drug.

SUMMARY

First aspect of the present application relates to a process for the preparation of compound of formula (I) comprising oxidation of chenodeoxycholic acid in presence of sodium hypochlorite, wherein oxidation is performed in absence of any additional oxidizing agent

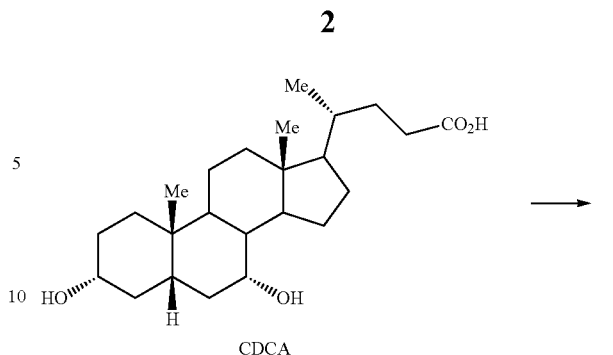

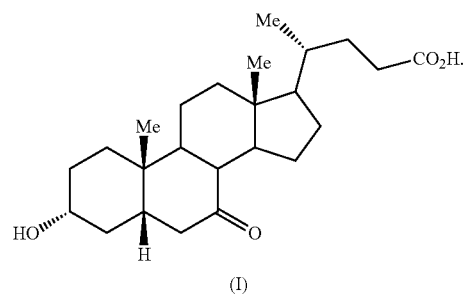

Second aspect of the present application relates to silylation of compound of formula (III) using an ionic additive, in the absence of a strong base to obtain compound of formula (IV)

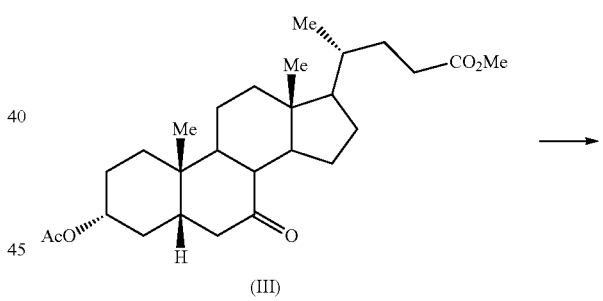

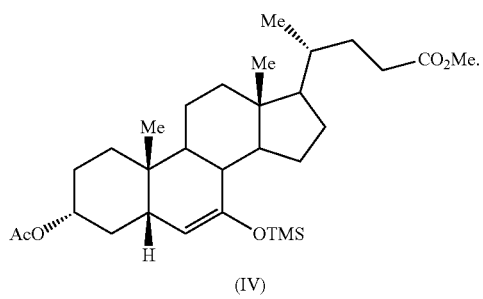

Third aspect of the present application relates to conversion of compound of formula (VI) to compound of formula (VII) using an organic base

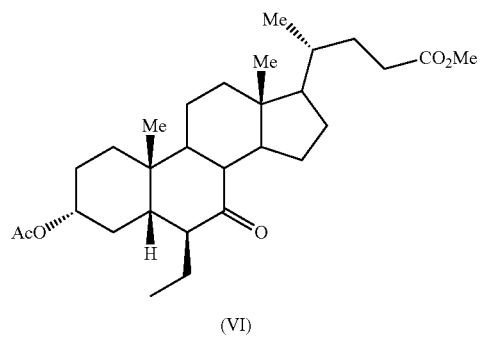

(VI)

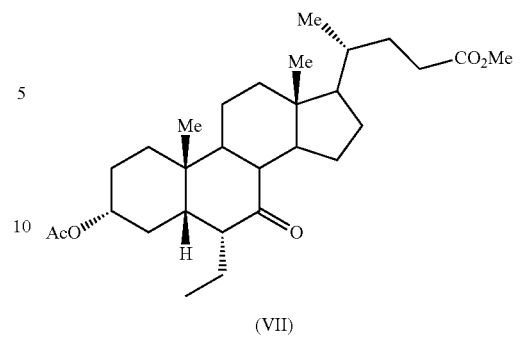

(VII)

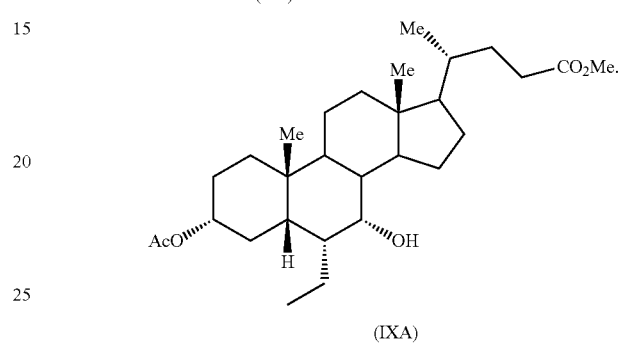

(VII)

Fourth aspect of the present application relates to deprotection of compound of formula (VII) to provide compound of formula (VIII)

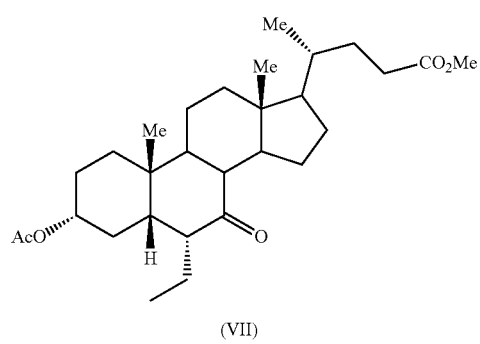

(VII)

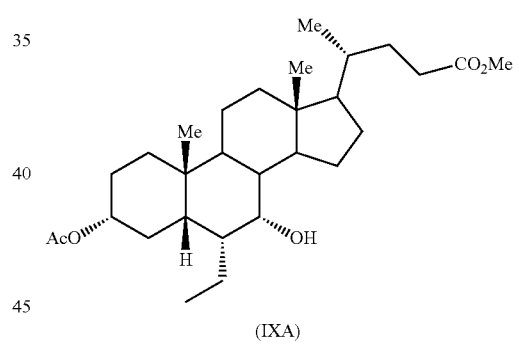

(IXA)

Sixth aspect of the present application relates to a process for preparation of obeticholic acid (X) comprising converting compound of formula (IXA) to obeticholic acid (X)

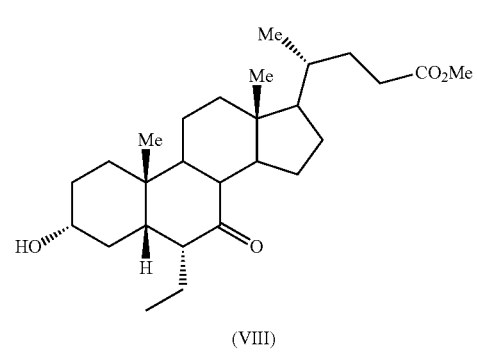

(VIII)

Fifth aspect of the present application relates to reduction of compound of formula (VII) to provide compound of formula (IXA) in presence of sodium borohydride

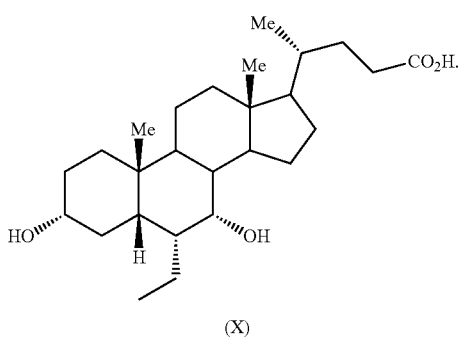

(X)

Seventh aspect of the present application relates to silylation of compound of formula (IIIA) using an ionic additive, in the absence of a strong base to obtain compound of formula (IVA)

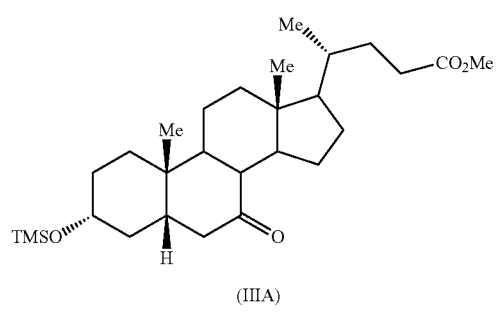

(IIIA)

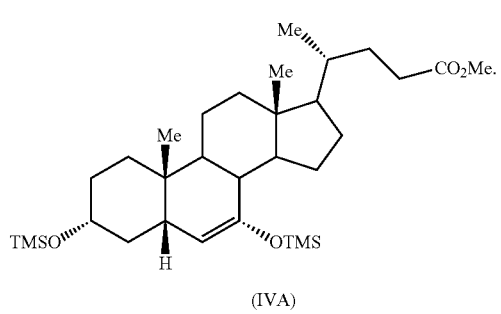

(IVA)

Eighth aspect of the present application relates to a process for preparation of compound of formula (V) comprising acetylation of compound of formula (VA)

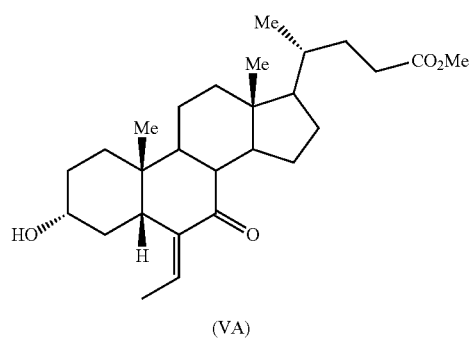

(VA)

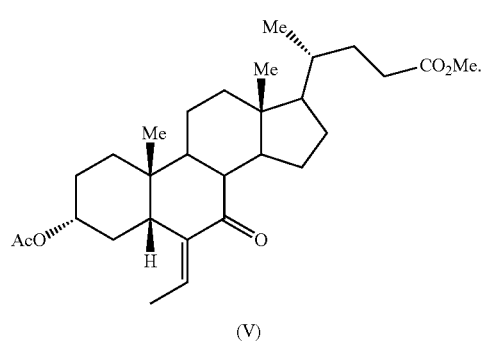

(V)

Ninth aspect of the present application relates to a process for the preparation of obeticholic acid (X) comprising the steps of:

a) conversion of compound of formula (VI) to compound of formula (VII) using an organic base

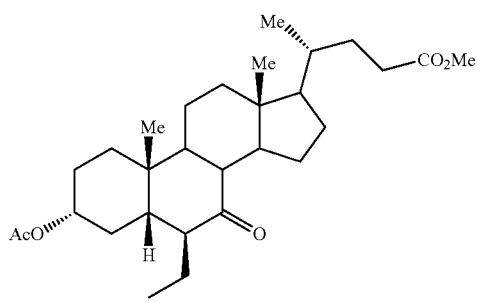

(VI)

(VII)

b) reduction of compound of formula (VII) to provide compound of formula (IXA) in presence of sodium borohydride

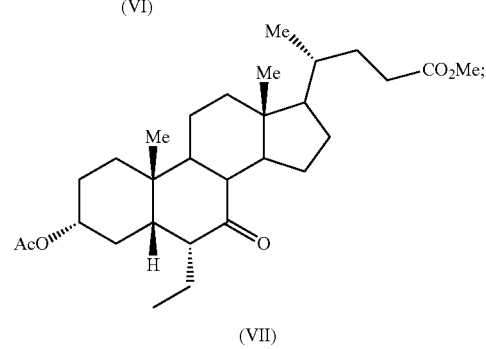

(VII)

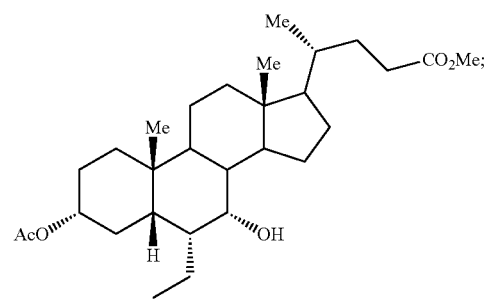

(IXA)

c) conversion of compound of formula (IXA) to obeticholic acid (X)

b) hydrogenation of compound of formula (V) to provide compound of formula (VI)

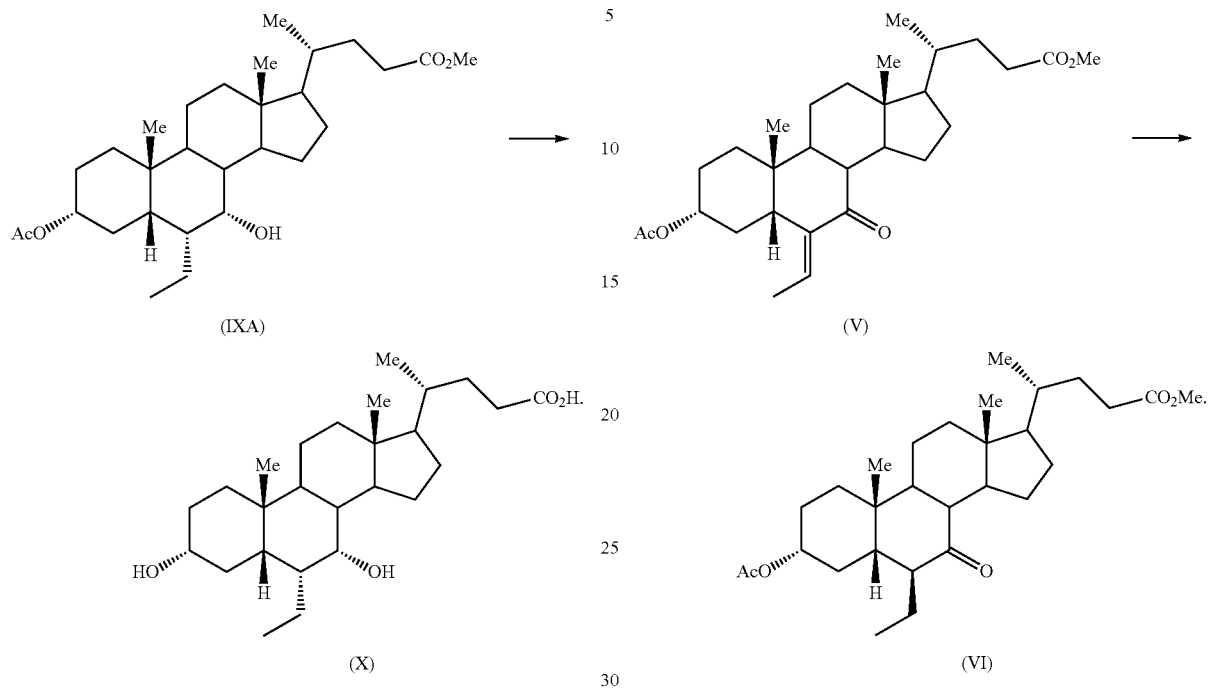

Tenth aspect of the present application relates to a process for the preparation of compound of formula (VI) comprising the steps of:

a) acetylation of compound of formula (VA) to provide compound of formula (V)

Eleventh aspect of the present application relates to a process for the preparation of obeticholic acid (X) comprising the steps of:

a) reduction of compound of formula (VII) to provide compound of formula (IXA) in presence of sodium borohydride

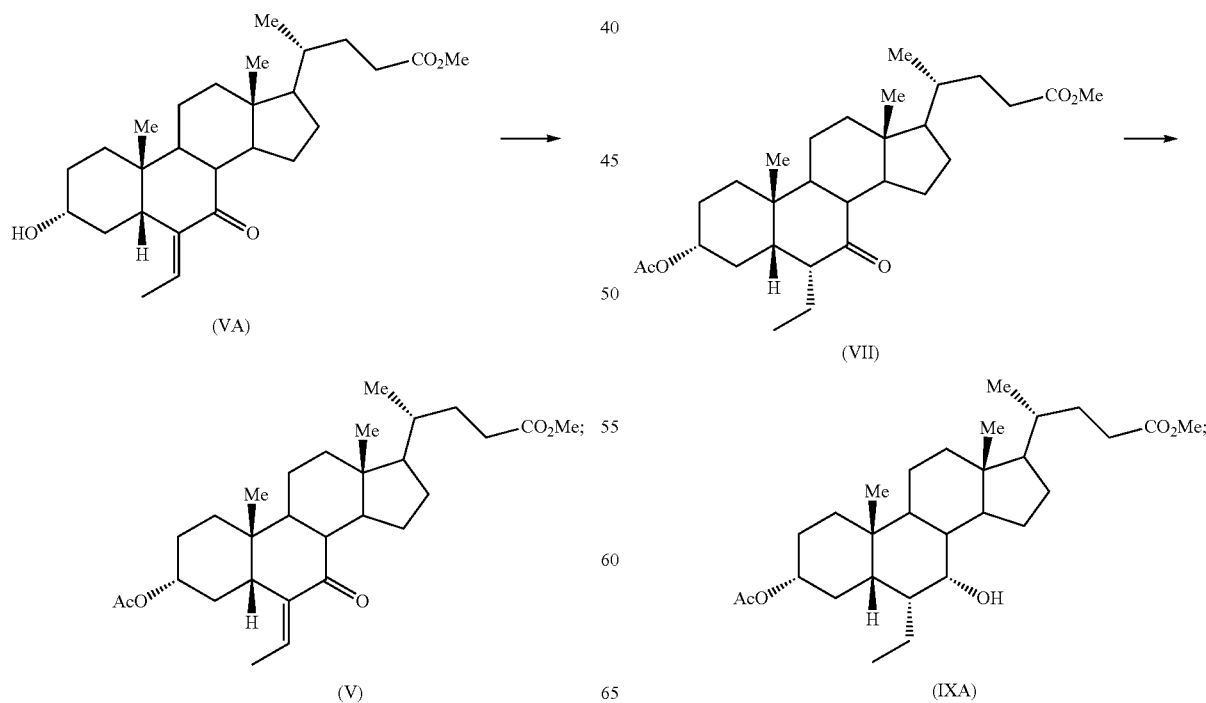

b) conversion of compound of formula (IXA) to obeticholic acid (X)

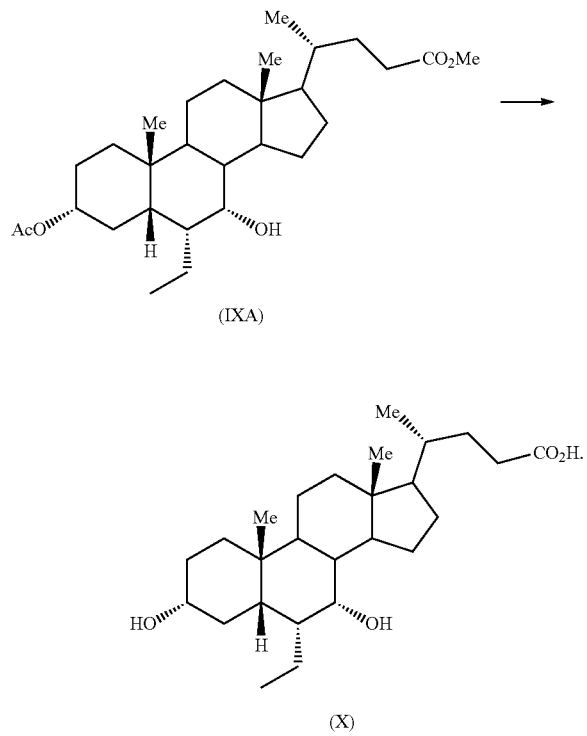

(IXA)

(X)

DETAILED DESCRIPTION

Figure 1:
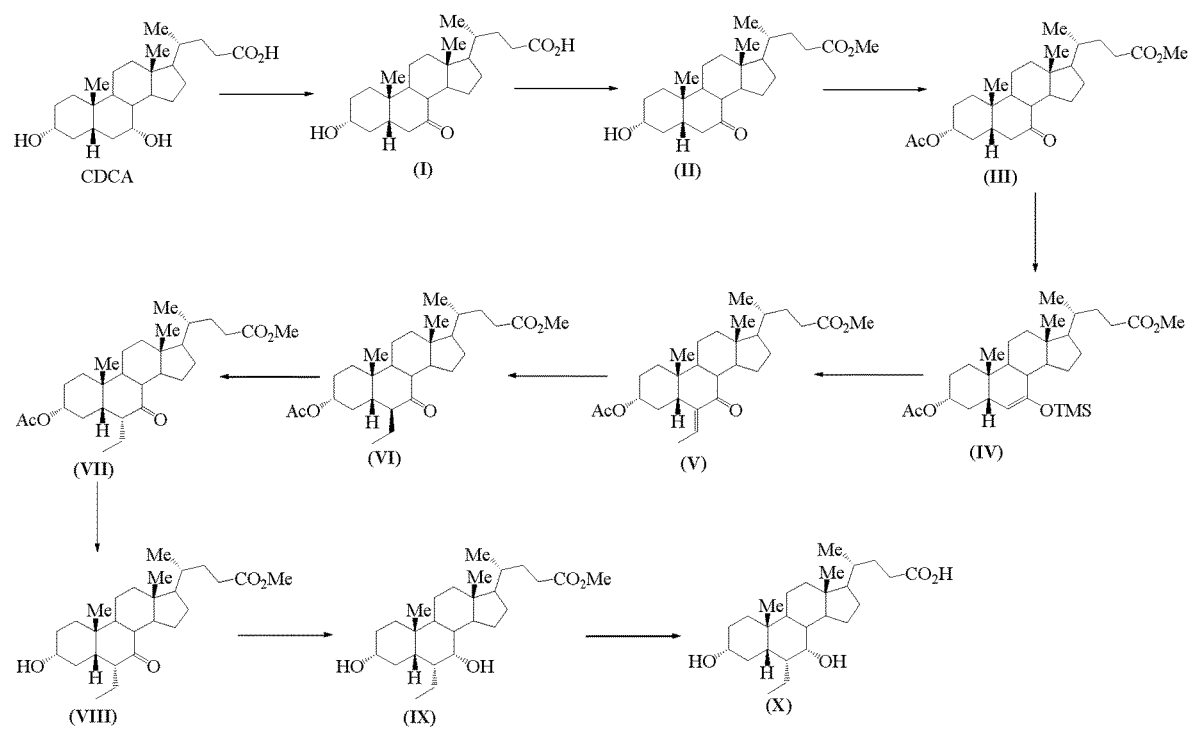
FIG. 1: Process I for preparation of obeticholic acid as described in the instant application
Figure 2:
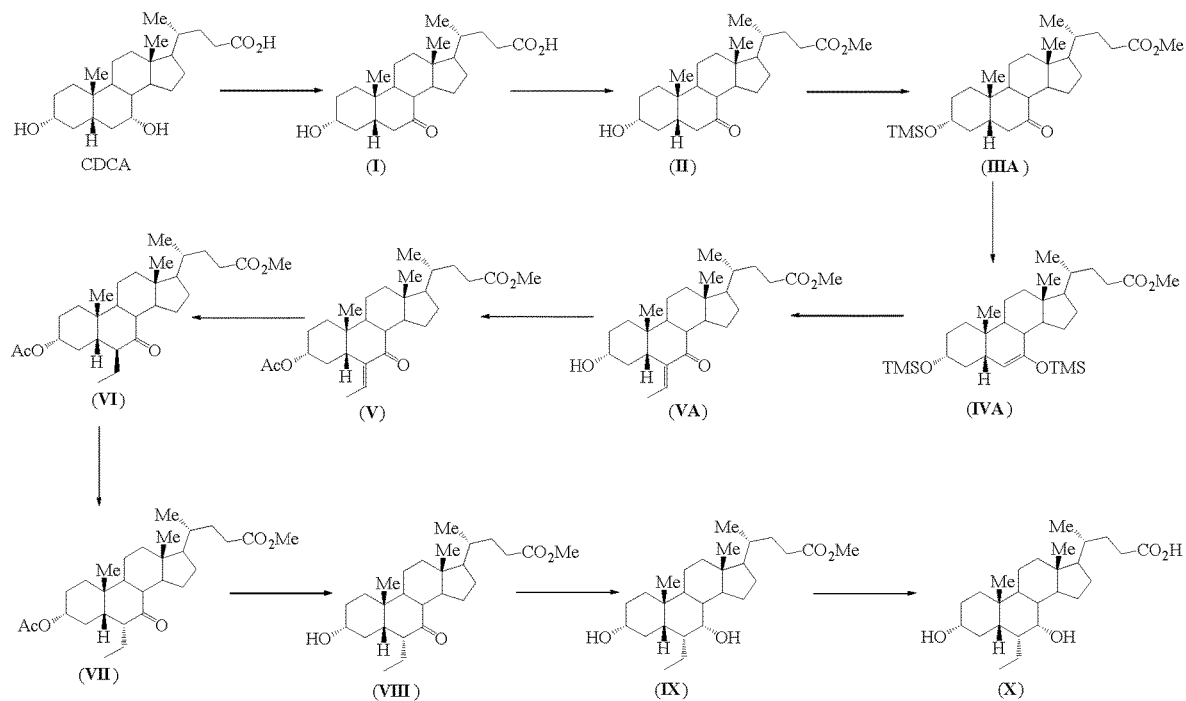
FIG. 2: Process II for preparation of obeticholic acid as described in the instant application
Figure 3:
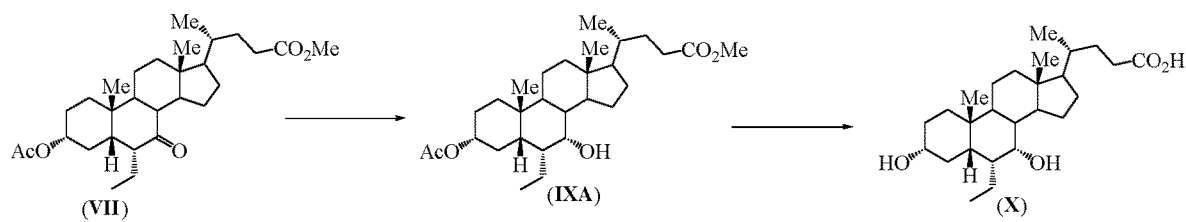
FIG. 3: Process III for preparation of obeticholic acid as described in the instant application

First aspect of the present application relates to a process for the preparation of compound of formula (I) comprising oxidation of chenodeoxycholic acid in presence of sodium hypochlorite, wherein oxidation is performed in absence of any additional oxidizing agent

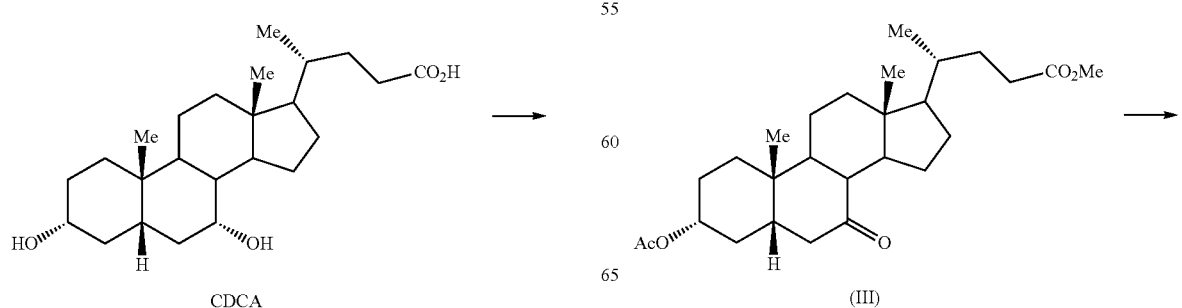

CDCA

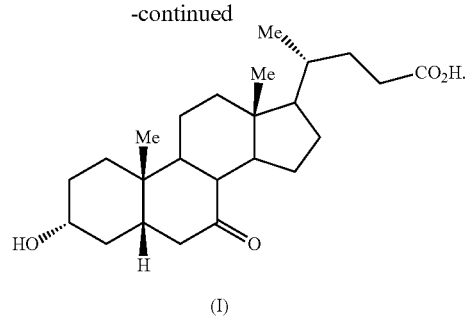

(I)

Sepe Valentina et al, J. Med. Chem., 2012, 55, 84-93 discloses a process for the preparation of 3α-hydroxy-7-keto-5β-cholanic acid (I) by oxidizing chenodeoxycholic acid in presence of sodium hypochlorite, sodium bromide and tert-butylammonium bromide.

The oxidation of chenodeoxycholic acid in presence of sodium hypochlorite, according to the process disclosed in this application, may be performed in presence of a suitable solvent, including but not limited to, alcoholic solvent such as methanol, ethanol, isopropanol and the like; ether such as tetrahydrofuran, diethyl ether and the like; esters such as ethyl acetate, n-butyl acetate and the like; polar protic solvents such as acetic acid, formic acid and the like; polar aprotic solvents such as dimethyl formamide, dimethyl sulfoxide and the like and mixtures thereof. Specifically, the solvent may be a mixture of an alcoholic solvent and a polar protic solvent. More specifically, the solvent may be a mixture of methanol and acetic acid. An aqueous solution of sodium hypochlorite may be added to a solution of chenodeoxycholic acid in a mixture of methanol and acetic acid. Alternatively, a solution of chenodeoxycholic acid in a mixture of methanol and acetic acid may be added to an aqueous solution of sodium hypochlorite. The addition may be performed at a controlled rate so that the temperature of the reaction mass remains constant. The reaction may be stirred for about 15 minutes to about 5 hours at about 20° C. to about 50° C. Specifically, the reaction may be stirred for about 30 minutes to about 1 hour at about 25° C. to about 35° C. The product may be isolated from the reaction by any known process in the art. Specifically, the product may be isolated from the reaction mass by filtration.

Second aspect of the present application relates to silylation of compound of formula (III) using an ionic additive, in the absence of a strong base to obtain compound of formula (IV)

(III)

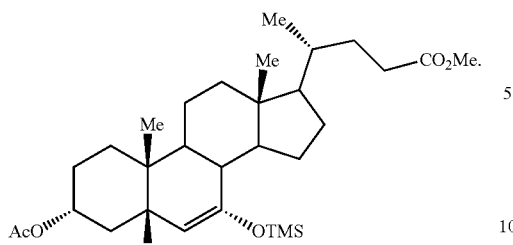

(IV)

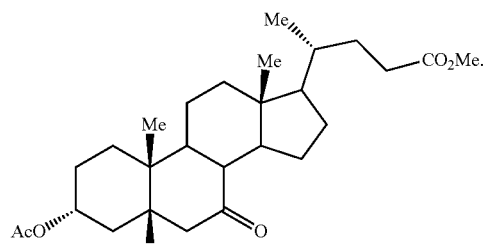

(III)

The US'352 patent teaches a process for the preparation of compound of formula (IV), which involves silylation of compound of formula (III) in presence of a strong base, such as an alkaline amide obtained from ammonia or an alkaline amide obtained from secondary aliphatic amine. The example of the US'352 patent discloses use of lithium diisopropylamide as the strong base.

The ionic additive may be any ionic additive known in the art. Specifically, the ionic additive may be an iodide salt of an alkali metal. More specifically, the ionic additive may be sodium iodide. Alternatively, the ionic additive may be potassium iodide. The solvent for silylation reaction includes but not limited to alcoholic solvents such as methanol, ethanol, isopropanol and the like; halogenated hydrocarbon solvent such as dichloromethane, carbon tetrachloride and the like; hydrocarbon solvent like heptane, hexane and the like; aromatic hydrocarbon solvent such as toluene, xylene and the like; ethers such as tetrahydrofuran, diethyl ether and the like; nitriles such as acetonitrile and the like. Specifically, the solvent may be a mixture of an aromatic hydrocarbon solvent and a nitrile solvent. More specifically, the solvent may be mixture of toluene and acetonitrile. Optionally, a weak base may be used for silylation reaction. The weak base may be any weak base known in the art. Specifically, the weak base may be an organic base. More specifically, the weak base may be triethylamine. The product, compound of formula (IV), may be isolated from the reaction mass by any known processes in the art. Alternatively, the reaction mass may be carried forward as such for the next reaction.

Compound of formula (III) may be prepared by any method known in the art. Specifically compound of formula (III) may be prepared from compound of formula (II) by a process disclosed in the PCT application, WO2015/181275

Compound of formula (II) may be prepared by any method known in the art. Specifically, compound of formula (II) may be prepared from compound of formula (I) by a process disclosed in the U.S. Pat. No. 9,238,673

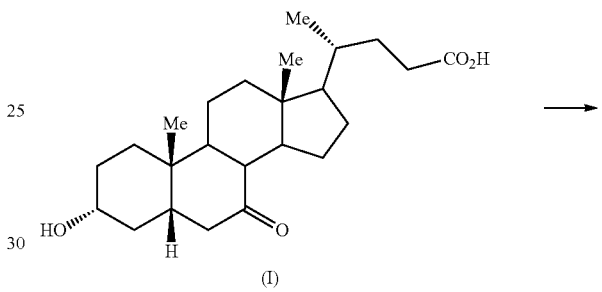

Third aspect of the present application relates to conversion of compound of formula (VI) to compound of formula (VII) using an organic base

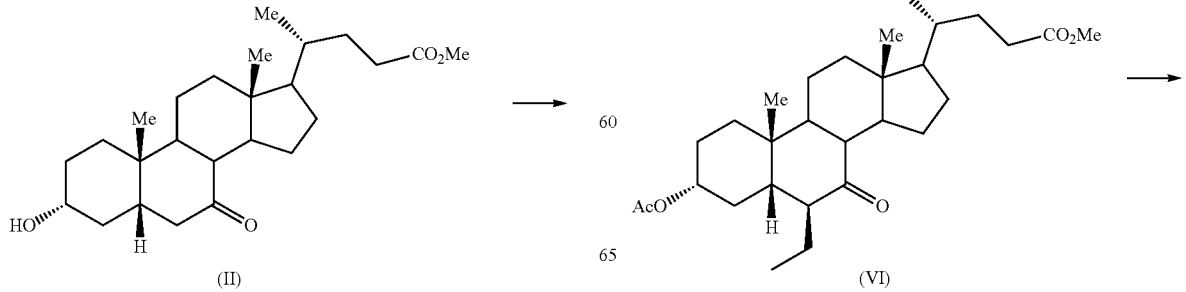

-continued

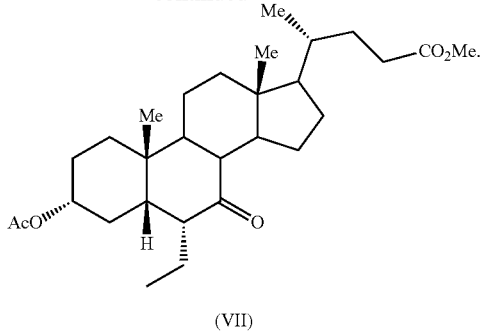

(VII)

The suitable solvent includes but not limited to alcoholic solvent such as methanol, ethanol and the like; ester solvent such as ethyl acetate, butyl acetate and the like; ether solvent such as tetrahydrofuran, diethyl ether and the like; ketone solvent such as acetone, methyl ethyl ketone and the like; aromatic hydrocarbon such as toluene, xylene and the like. Specifically, the solvent may be an aromatic hydrocarbon solvent. More specifically, the solvent may be toluene. The suitable organic base may be any organic base known in the art. The suitable organic base includes but not limited to triethylamine, N-methyl pyrrolidone, 1,4-diazabicyclo[2.2.2]octane, pyridine, 1,8-diazabicyclo[5.4.0]undec-7-ene, N,N-diisopropylethylamine, diethylamine, hexylamine, 2,6-lutidine, piperidine, morpholine and the like. Specifically, the suitable organic base may be 1,8-diazabicyclo[5.4.0]undec-7-ene. The reaction may be performed at about 0° C. to about boiling point of the solvent for about 1 hour to about 20 hours. The product may be isolated from the reaction mass by any suitable technique known in the art.

Compound of formula (V) may be reduced by hydrogen gas in presence of a heterogeneous catalyst to provide compound of formula (VI). Specifically, compound of formula (V) may be reduced to provide compound of formula (VI), as described in the PCT application, WO2015/181275

Compound of formula (V) may be prepared by a process known in the art from a compound of formula (IV). Specifically, the compound of formula (IV) may be reacted with acetaldehyde in presence of a Lewis acid to provide compound of formula (V), as described in the PCT application, WO2015/181275

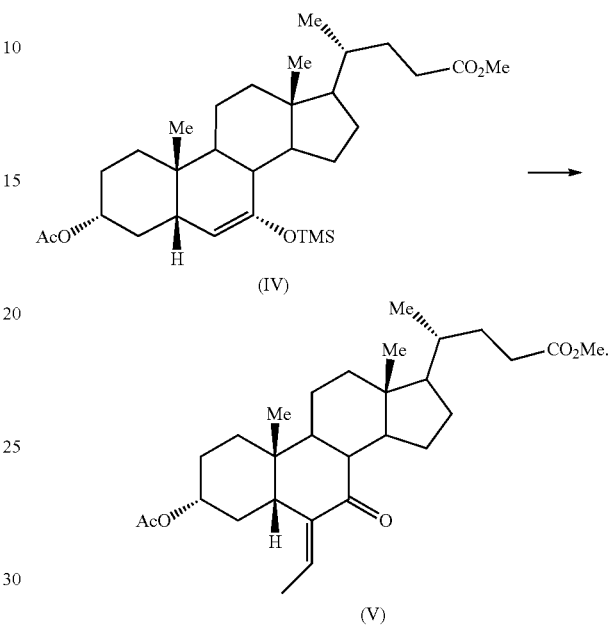

Fourth aspect of the present application relates to deprotection of compound of formula (VII) to provide compound of formula (VIII)

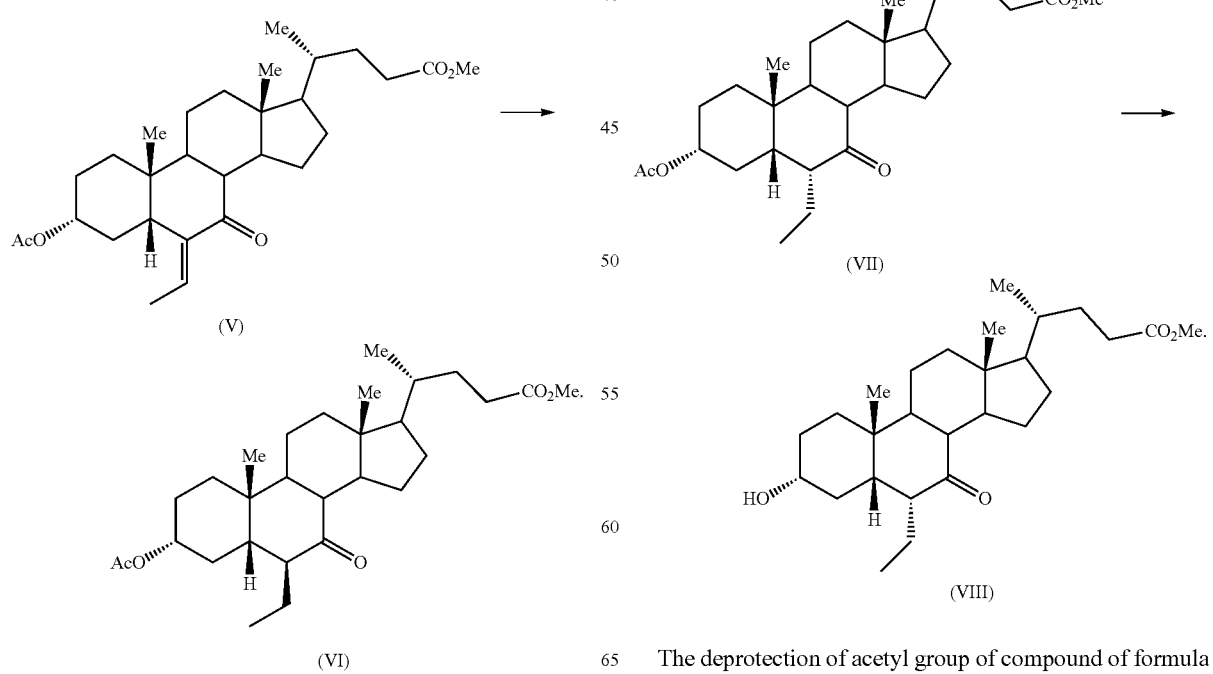

The deprotection of acetyl group of compound of formula (VII) may be performed in presence of an acid. The suitable acid may be selected from an organic acid such as oxalic acid, methane sulfonic acid and the like; and an inorganic acid such as hydrochloric acid, sulfuric acid and the like. Alternatively, the deprotection of acetyl group of compound of formula (VII) may be performed in presence of a base. The suitable base may be selected from a group of hydroxide base such as sodium hydroxide, potassium hydroxide and the like; carbonate base such as sodium carbonate, potassium carbonate and the like; bicarbonate base such as sodium bicarbonate, potassium bicarbonate and the like. Specifically, the deprotection of acetyl group of compound of formula (VII) may be performed in presence of an acid. More specifically, the deprotection of acetyl group of compound of formula (VII) may be performed in presence of sulfuric acid.

The suitable solvent includes but not limited to alcohol solvent such as methanol, ethanol and the like; ketone solvent such as acetone, methyl iso-butyl ketone and the like; ester solvent such as ethyl acetate, butyl acetate and the like; aliphatic hydrocarbon solvent such as heptane, hexane, cyclopentane and the like; aromatic hydrocarbon solvent such as toluene, benzene and the like. Specifically, the solvent may be an alcohol solvent. More specifically, the solvent may be methanol. The reaction may be performed at about 0° C. to about boiling point of the solvent for about 1 hour to about 20 hours. Specifically, reaction may be performed at about 30° C. to about 60° C. for about 2 hours to about 10 hours. The product may be isolated from the reaction mass by any suitable technique known in the art.

Compound of formula (VIII) may be converted to obeticholic acid by a process as disclosed in the WO'598 application. Specifically, the compound of formula (VIII) may be converted to compound of formula (IX) in presence of sodium borohydride

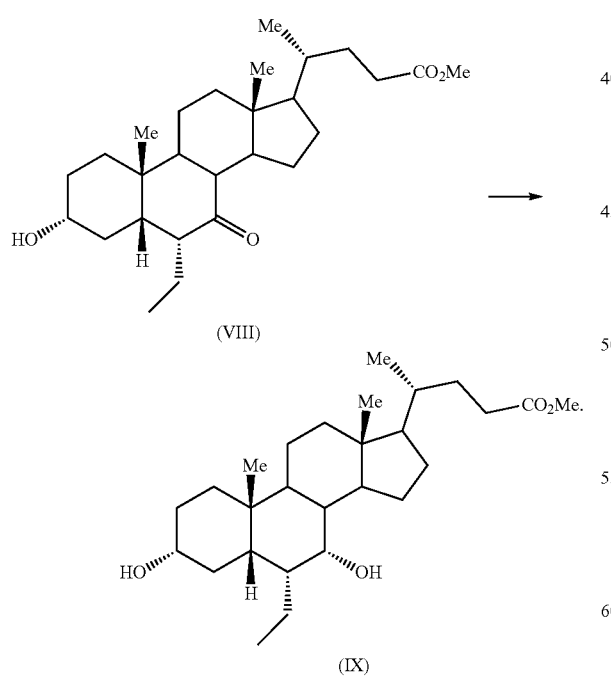

Compound of formula (IX) may be hydrolyzed in presence of a base, as known in the WO'598 application to provide obeticholic acid (X)

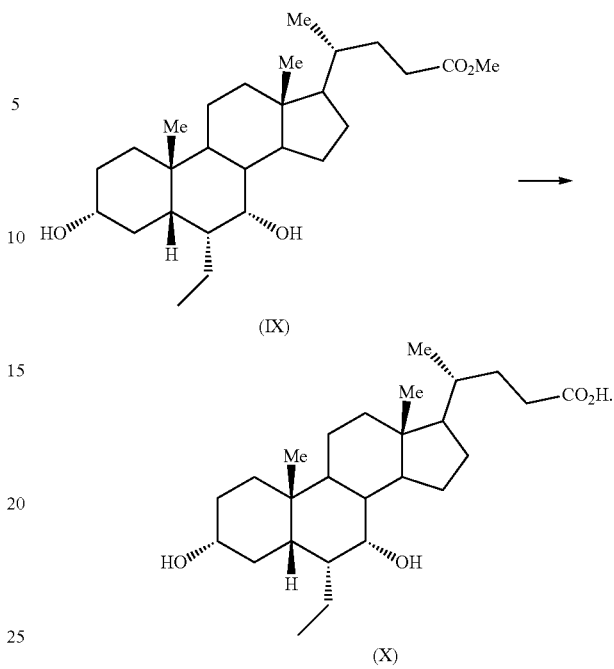

Fifth aspect of the present application relates to reduction of compound of formula (VII) to provide compound of formula (IXA) in presence of sodium borohydride

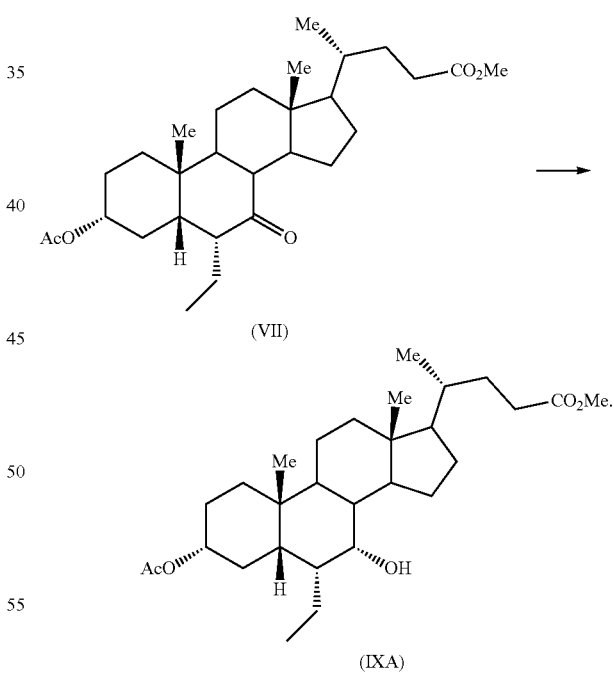

The reduction of compound of formula (VII) to provide compound of formula (IXA) in presence of sodium borohydride may be carried out in an organic solvent including but not limited to alcohol solvent such as methanol, ethanol and the like; ether solvent such as diethyl ether, tetrahydrofuran and the like; aliphatic hydrocarbon solvent such as cyclohexane, n-heptane and the like; aromatic hydrocarbon solvent such as xylene, toluene and the like or mixture thereof. Specifically, the reduction of compound of formula (VII) to provide compound of formula (IXA) in presence of sodium borohydride may be carried out in a mixture of an alcohol solvent and an ether solvent. More specifically, the reduction of compound of formula (VII) to provide compound of formula (IXA) in presence of sodium borohydride may be carried out in a mixture of methanol and tetrahydrofuran. The product may be isolated from the reaction mass by any suitable technique known in the art.

Sixth aspect of the present application relates to a process for preparation of obeticholic acid (X) comprising converting compound of formula (IXA) to obeticholic acid (X) Me,

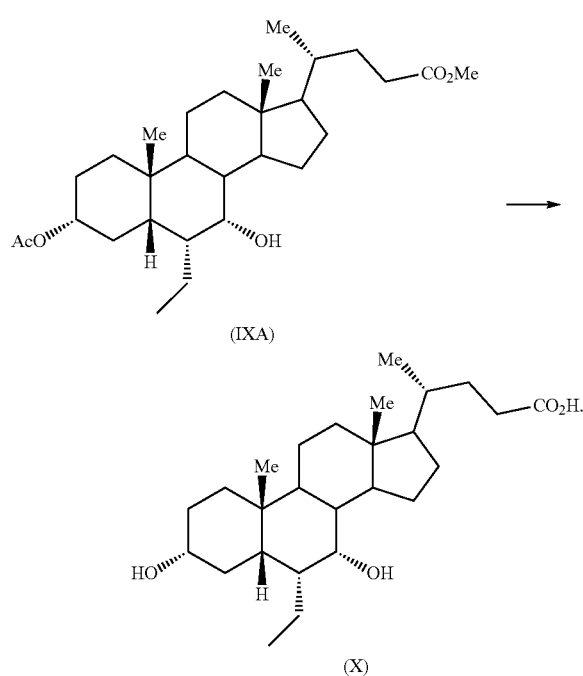

The compound of formula (IXA) may be reacted with a base or an acid to provide obeticholic acid (X) in one or more than one step. Specifically, compound of formula (IXA) may be reacted with a base to provide obeticholic acid (X) in one step. The suitable base may include but not limited to organic base such as pyridine, diisopropyl ethylamine, triethylamine and the like; inorganic base such as sodium hydroxide, potassium hydroxide, sodium carbonate, potassium carbonate, sodium bicarbonate, potassium bicarbonate and the like. Specifically, the base may be an inorganic base. More specifically, the base may be sodium hydroxide. The solvent may include but not limited to alcohol solvent such as methanol, ethanol and the like; ether solvent such as tetrahydrofuran, diethyl ether and the like; water; ketone solvent such as acetone, methyl ethyl ketone and the like and mixture thereof. Specifically, the solvent may be a mixture of an alcohol solvent and water. More specifically, the solvent may be a mixture of methanol and water. The product may be isolated from the reaction mass by any suitable technique known in the art.

Seventh aspect of the present application relates to silylation of compound of formula (IIIA) using an ionic additive, in the absence of a strong base to obtain compound of formula (IVA)

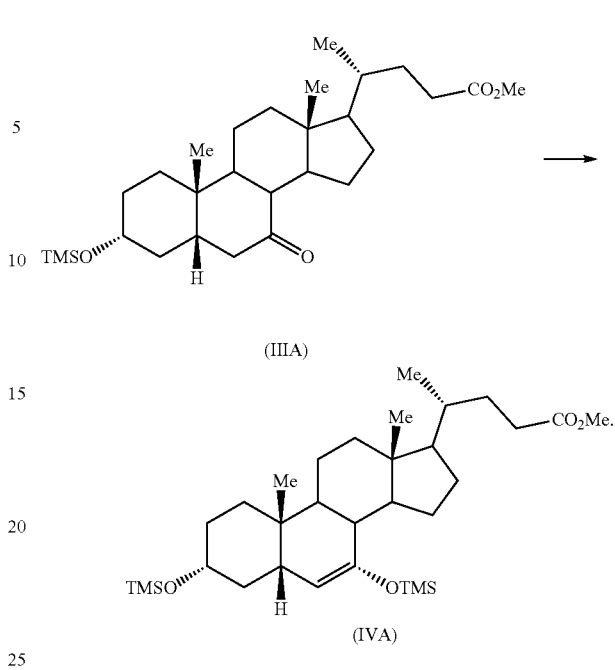

The compound of formula (IIIA) may be prepared as known in the art. Specifically, the compound of formula (IIIA) may be from compound of formula (II) as known in the US'352 patent.

The US'352 patent teaches a process for the preparation of compound of formula (IVA), which involves silylation of compound of formula (IIIA) in presence of a strong base, such as an alkaline amide obtained from ammonia or an alkaline amide obtained from secondary aliphatic amine. The example of the US'352 patent discloses use of lithium diisopropylamide as the strong base.

The ionic additive may be any ionic additive known in the art. Specifically, the ionic additive may be an iodide salt of an alkali metal. More specifically, the ionic additive may be sodium iodide. Alternatively, the ionic additive may be potassium iodide. The solvent for silylation reaction includes but not limited to alcoholic solvents such as methanol, ethanol, isopropanol and the like; halogenated hydrocarbon solvent such as dichloromethane, carbon tetrachloride and the like; hydrocarbon solvent like heptane, hexane and the like; aromatic hydrocarbon solvent such as toluene, xylene and the like; ethers such as tetrahydrofuran, diethyl ether and the like; nitriles such as acetonitrile and the like. Specifically, the solvent may be a mixture of an aromatic hydrocarbon solvent and a nitrile solvent. More specifically, the solvent may be mixture of toluene and acetonitrile. Optionally, a weak base may be used for silylation reaction. The weak base may be any weak base known in the art. Specifically, the weak base may be an organic base. More specifically, the weak base may be triethylamine. The product, compound of formula (IVA), may be isolated from the reaction mass by any known processes in the art. Alternatively, the reaction mass may be carried forward as such for the next reaction.

An alternative aspect of the present application relates to the conversion of compound of formula (II) to the compound of formula (IVA) using an ionic additive, in the absence of a strong base, wherein the compound of formula (IIIA) may be an in-situ intermediate.

Eighth aspect of the present application relates to a process for preparation of compound of formula (V) comprising acetylation of compound of formula (VA)

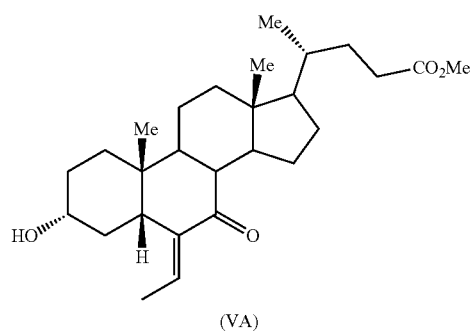

(VA)

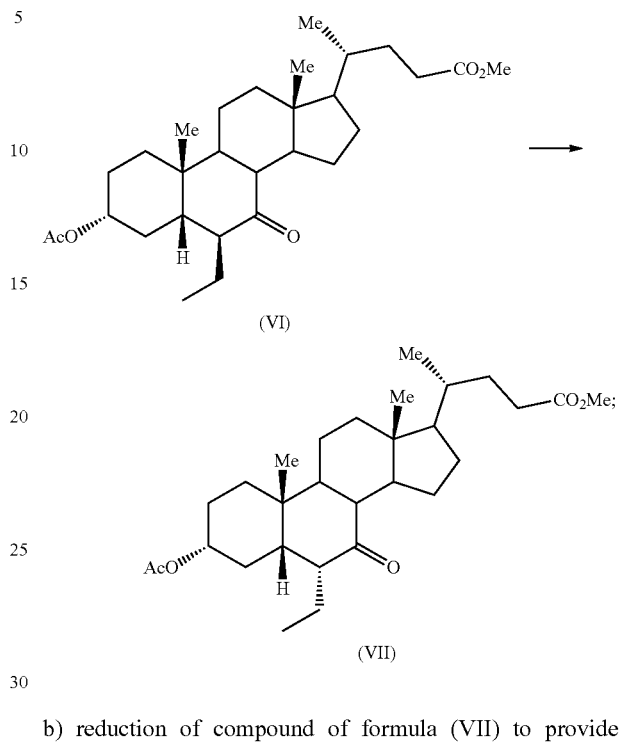

a) conversion of compound of formula (VI) to compound of formula (VII) using an organic base (VI)

(VII)

b) reduction of compound of formula (VII) to provide compound of formula (IXA) in presence of sodium borohydride

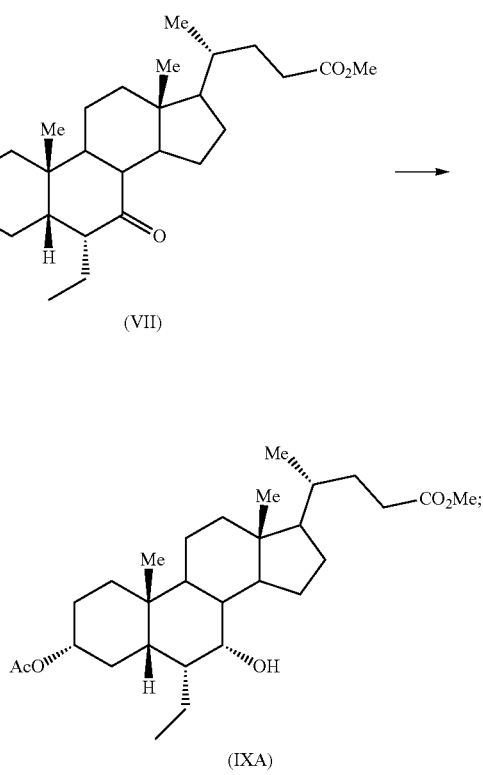

(VII)

(IXA)

(V)

The acetylation of compound of formula (VA) may be performed by reacting with acetic anhydride in a solvent including but not limited to ketone solvent such as acetone, methyl isobutyl ketone and the like; ether solvent such as diethyl ether, tetrahydrofuran and the like; aliphatic hydrocarbon solvent such as n-hexane, n-heptane and the like; aromatic hydrocarbon solvent such as toluene, benzene and the like, chlorinated hydrocarbon solvent such as dichloromethane, chloroform and the like. Specifically, the solvent may be an chlorinated hydrocarbon solvent. Specifically, the solvent may be dichloromethane. Optionally, the acetylation of compound of formula (VA) may be performed in presence of a catalyst. The catalyst may be any catalyst known in the art. Specifically, the catalyst may be dimethyl amino pyridine. The product, compound of formula (V), may be isolated from the reaction mass by any known processes in the art. Alternatively, the reaction mass may be carried forward as such for the next reaction.

The compound of formula (VA) may be obtained from a compound of formula (IVA) by a process known in the art. Specifically, the compound of formula (VA) may be obtained from a compound of formula (IVA) by a process as known in the US'352 patent.

Ninth aspect of the present application relates to a process for the preparation of obeticholic acid (X) comprising the steps of:

c) conversion of compound of formula (IXA) to obeticholic acid (X)

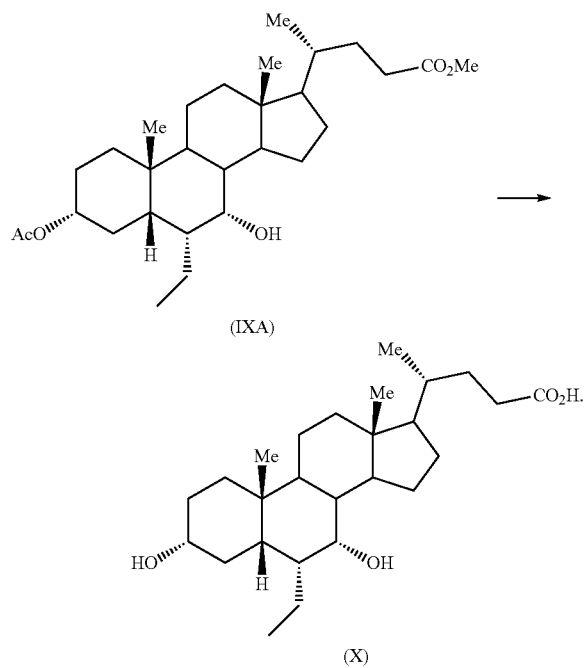

In embodiment of step a), the reaction may be carried out in a suitable solvent including but not limited to ether solvent such as tetrahydrofuran, diethyl ether and the like; hydrocarbon solvent such as hexane, heptane and the like; aromatic hydrocarbon such as toluene, xylene and the like. Specifically, the solvent may be an aromatic hydrocarbon solvent. More specifically, the solvent may be toluene. The suitable organic base in step a) includes but not limited to triethylamine, 1,4-diazabicyclo[2.2.2]octane, 1,8-diazabicyclo[5.4.0]undec-7-ene and the like. Specifically, the suitable organic base may be 1,8-diazabicyclo[5.4.0]undec-7-ene. The reaction of step a) may be performed at about 0° C. to about boiling point of the solvent for about 1 hour to about 20 hours. Specifically, the reaction of step a) may be carried out at about boiling point of the solvent for about 5 hours to about 18 hours. The product may be isolated from the reaction mass by any suitable technique known in the art.

In embodiments of step b), reduction of compound of formula (VII) to provide compound of formula (IXA) in presence of sodium borohydride may be carried out in an organic solvent including but not limited to alcohol solvent such as methanol, ethanol and the like; ether solvent such as diethyl ether, tetrahydrofuran and the like; aromatic hydrocarbon solvent such as xylene, toluene and the like or mixture thereof. Specifically, the reduction may be carried out in a mixture of an alcohol solvent and an ether solvent. More specifically, the reduction may be carried out in a mixture of methanol and tetrahydrofuran. The reaction of step b) may be performed at about 0° C. to about 5° C. for about 1 hour to about 4 hours. The product may be isolated from the reaction mass by any suitable technique known in the art.

In embodiments of step c), conversion of compound of formula (IXA) to obeticholic acid (X) may be carried out in presence of a base or an acid in one or more than one step. Specifically, compound of formula (IXA) may be reacted with a base to provide obeticholic acid (X) in one step. The suitable base may include but not limited to organic base such as diisopropyl ethylamine, triethylamine and the like; inorganic base such as sodium hydroxide, potassium hydroxide, sodium carbonate and the like. Specifically, the base may be an inorganic base. More specifically, the base may be sodium hydroxide. The solvent used in step c) may include but not limited to alcohol solvent such as methanol, ethanol and the like; ether solvent such as tetrahydrofuran, diethyl ether and the like; water and mixture thereof. Specifically, the solvent may be a mixture of an alcohol solvent and water. More specifically, the solvent may be a mixture may be methanol and water. The reaction of step c) may be performed at about 0° C. to about boiling point of the solvent for about 30 minutes to about 5 hours. Specifically, the reaction of step c) may be performed at about 40° C. to about boiling point of the solvent for about 1 hour to about 3 hours. The product may be isolated from the reaction mass by any suitable technique known in the art.

One specific aspect of the present application relates to use of compound of formula (VI) for the preparation of obeticholic acid (X). Another specific aspect of the present application relates to a process for preparing obeticholic acid (X) comprising using compound of formula (VI) as an intermediate.

One specific aspect of the present application relates to use of compound of formula (VII) for the preparation of obeticholic acid (X). Another specific aspect of the present application relates to a process for preparing obeticholic acid (X) comprising using compound of formula (VII) as an intermediate. Yet another specific aspect of the present application relates to a process for preparation of obeticholic acid comprising the step of conversion of compound of formula (VI) to compound of formula (VII) using an organic base.

One specific aspect of the present application relates to use of compound of formula (IXA) for the preparation of obeticholic acid (X). Another specific aspect of the present application relates to a process for preparing obeticholic acid (X) comprising using compound of formula (IXA) as an intermediate. Yet another specific aspect of the present application relates to a process for preparation of obeticholic acid comprising the step of reduction of compound of formula (VII) to provide compound of formula (IXA) in presence of sodium borohydride.

Tenth aspect of the present application relates to a process for the preparation of compound of formula (VI) comprising the steps of:

a) acetylation of compound of formula (VA) to provide compound of formula (V)

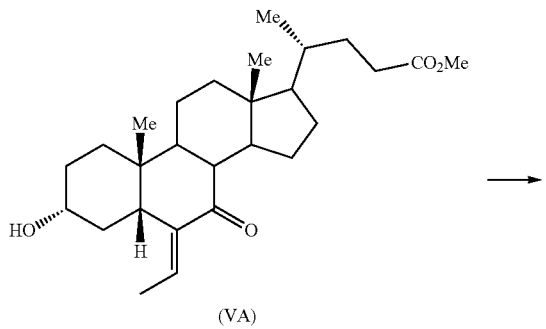

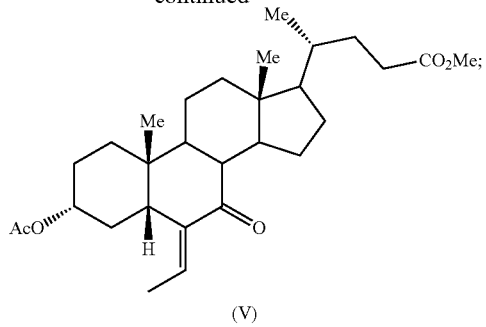

(V)

b) hydrogenation of compound of formula (V) to provide compound of formula (VI)

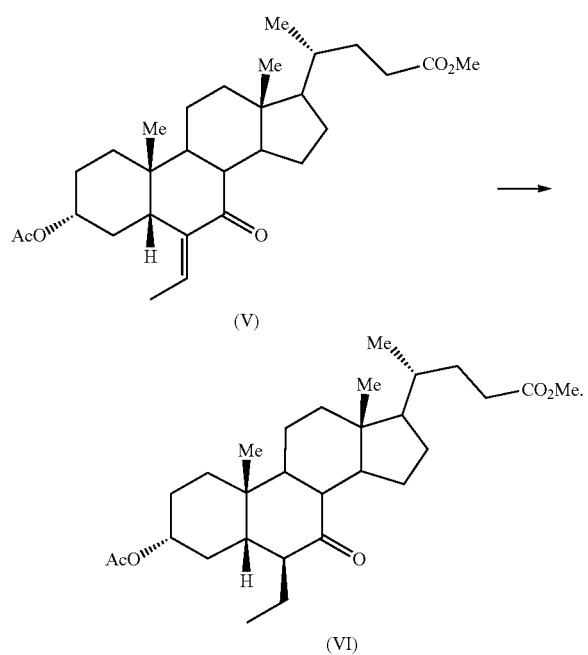

In embodiments of step a), acetylation of compound of formula (VA) may be performed by reacting with acetic anhydride in a solvent including but not limited to ether solvent such as diethyl ether, tetrahydrofuran and the like; aromatic hydrocarbon solvent such as toluene, benzene and the like, chlorinated hydrocarbon solvent such as dichloromethane, chloroform and the like. Specifically, the solvent may be chlorinated hydrocarbon solvent. Specifically, the solvent may be dichloromethane. Optionally, the acetylation of compound of formula (VA) may be performed in presence of a catalyst. The catalyst may be any catalyst known in the art. Specifically, the catalyst may be dimethyl amino pyridine. The product, compound of formula (V), may be isolated from the reaction mass by any known processes in the art. Alternatively, the reaction mass may be carried forward as such for the next reaction.

In embodiments of step b), hydrogenation may be carried out by any process known in the art. Specifically, hydrogenation may be carried out by a process as described in WO2015/181275.

One specific aspect of the present application relates to use of compound of formula (V) for the preparation of obeticholic acid (X). Another specific aspect of the present application relates to a process for preparing obeticholic acid (X) comprising using compound of formula (V) as an intermediate. Yet another specific aspect of the present application relates to a process for preparation of obeticholic acid comprising the step of acetylation of compound of formula (VA) to provide compound of formula (V).

One specific aspect of the present application relates to use of compound of formula (VA) for the preparation of obeticholic acid (X). Another specific aspect of the present application relates to a process for preparing obeticholic acid (X) comprising using compound of formula (VA) as an intermediate.

Eleventh aspect of the present application relates to a process for the preparation of obeticholic acid (X) comprising the steps of:

a) reduction of compound of formula (VII) to provide compound of formula (IXA) in presence of sodium borohydride

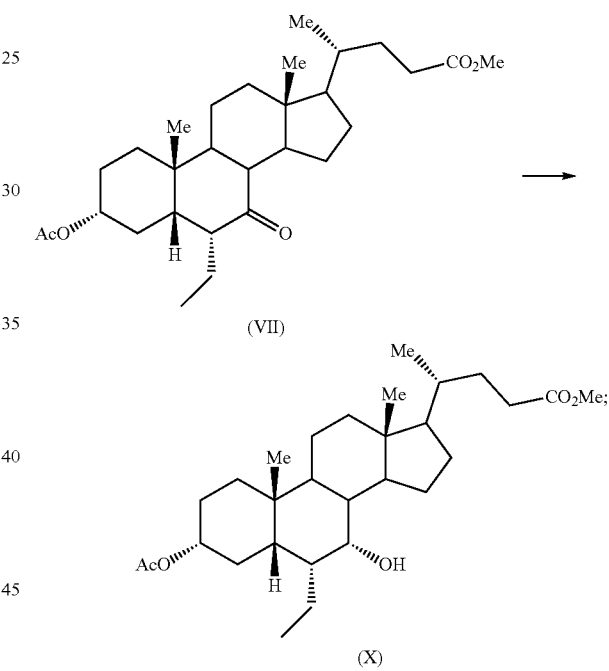

b) conversion of compound of formula (IXA) to obeticholic acid (X)

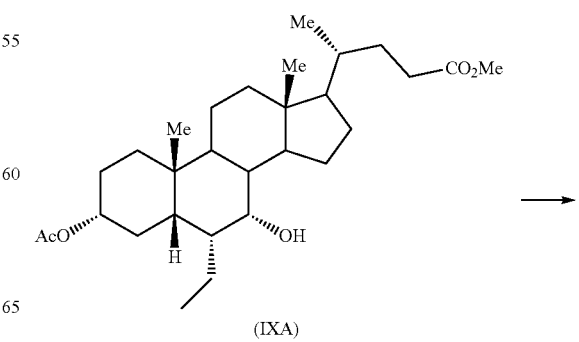

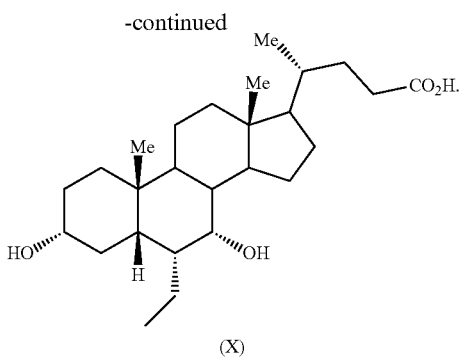

(X)

The process for the preparation of obeticholic acid, as described in the instant application, is simple, economic and industrially viable process.

DEFINITIONS

The following definitions are used in connection with the present application unless the context indicates otherwise.

The terms "about," "general, 'generally," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

All percentages and ratios used herein are by weight of the total composition and all measurements made are at about 25° C. and about atmospheric pressure, unless otherwise designated. All temperatures are in degrees Celsius unless specified otherwise. As used herein, the terms "comprising" and "comprises" mean the elements recited, or their equivalents in structure or function, plus any other element or elements which are not recited. The terms "having" and "including" are also to be construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term "room temperature" is taken to mean a temperature of about 20° C. to about 30° C.

The term "optional" or "optionally" is taken to mean that the event or circumstance described in the specification may or may not occur, and that the description includes instances where the event occurs and instances where it does not.

The term "Crude" is taken to mean that the material is not pure enough to be used as drug. The term TMS is taken to mean "trimethyl silyl" group. The term "—OAc" is taken to mean "acetyloxy" group.

Certain specific aspects and embodiments of the present application will be explained in greater detail with reference to the following examples, which are provided only for purposes of illustration and should not be construed as limiting the scope of the disclosure in any manner.

EXAMPLES

Example 1: Preparation of 3α-hydroxy-7-keto-5β-cholanic Acid (I)

A mixture of chenodeoxycholic acid (100 g) in methanol (500 mL) and acetic acid (100 mL) was stirred for 10 minutes at about 30° C. An aqueous solution of sodium hypochlorite (12.97% w/v, 124.2 mL) was added to the above solution drop wise in such a way that the temperature of the reaction mass remains constant. The reaction mass was stirred for 1 hour at 28° C. and charged an aqueous solution of sodium hypochlorite (12.97% w/v, 75 mL) and stirred for one hour. To the reaction mass then slowly added aqueous sodium bisulfite solution (53.06 g in 500 mL water). The reaction mass was stirred for about 1 hour at 31° C. Water (2000 mL) was added to the reaction mass and further stirred for 1 hour at 25-35° C. The solid was filtered and washed with water (1000 mL). The solid was dried under suction over Buchner funnel for about 60 minutes. The wet solid was dried under vacuum at about 70° C. for 6 hours to provide the desired compound.

Yield: 88.7 g
Purity (by HPLC): 89.16%

Example 2: Preparation of Methyl 3α-hydroxy-7-keto-5β-cholanate (II)

To a mixture of 3α-hydroxy-7-keto-5β-cholanic acid (I) (80 g) and methanol (400 mL), concentrated sulphuric acid (1.6 mL) was added slowly under nitrogen atmosphere at 25-35° C. The reaction mass was stirred for 24 hours at 25-35° C. Triethylamine (9.6 mL) was added to the reaction mass and the reaction mass was stirred for 10-20 minutes. The aqueous solution of sodium bicarbonate (4%, 800 mL), was added to the reaction mass drop wise over a period of 3 hours and continued stirring for one hour and then filtered and washed with water. The wet solid was mixed with ethyl acetate (120 mL) and heated to 45° C. The reaction mass was stirred for 10-20 minutes at 40-50° C. and cooled to 25-35° C. Brine (40 mL) was added to the reaction mass and the reaction mass was stirred for 10-20 minutes at 27° C. The organic layer was separated and hexane (1200 mL) was added to it slowly over a period of 3 hours. The reaction mass was stirred for 1 hour at 27° C. and filtered. The solid was washed with 5% ethyl acetate in hexanes mixture (160 mL). The solid was dried under vacuum at about 45° C. for 8-10 hours to afford the desired compound.

Yield: 67.25 g
Purity (by HPLC): 81.15%

Example 3: Preparation of Methyl 3α-acetoxy-7-keto-5β-cholanate (III)

To a mixture of methyl 3α-hydroxy-7-keto-5β-cholanate (25 g) (II) and dichloromethane (250.0 mL), triethyl amine (12.51 g) and catalytic amount of dimethyl aminopyridine (0.755 g) were added under nitrogen atmosphere at 26° C. Acetic anhydride (7.75 g) was added slowly to the above reaction mass and stirred under nitrogen for 1-2 hours. Another lot of acetic anhydride (1.26 mL) was added to the reaction mass and stirred under nitrogen for about 2 hours. Saturated sodium bicarbonate solution (125 mL) was added to the reaction mass and the organic layer was separated. Aqueous layer was further extracted with dichloromethane (125 mL) and combined organic layers were concentrated under vacuum. The obtained residue was slurried in methanol (50 mL), filtered, washed with methanol (25 mL) and dried under vacuum to afford title product.

Yield: 25.8 g

Example 4: Preparation of Methyl 3α-acetoxy-7-trimethylsilyloxy-5β-cholanate (IV)

Triethyl amine (9.06 g) was added to a suspension of sodium iodide (10.07 g) in acetonitrile (50 mL) followed by solution of methyl 3α-acetoxy-7-keto-5β-cholanate (III) (10.0 g) in toluene (50 mL). Trimethyl silyl chloride (7.3 g) was added slowly under nitrogen atmosphere to the reaction mass. The temperature of the reaction mass was raised to 52° C. and stirred for 5 hours. The reaction mass was quenched in an aqueous solution of sodium thiosulphate (2.5 g), sodium bicarbonate (4.0 g) in water (50 mL). The aqueous layer was separated and extracted with toluene (50 mL). The organic layers were combined and completely distilled under vacuum to provide the desired compound.

Yield: 12.7 g

Example 5: Preparation of Methyl 3α-acetoxy-6-ethylidene-7-keto-5β-cholanate (V)

To a suspension of methyl 3α-acetoxy-7-trimethylsilyloxy-5β-cholanate (IV) (5.0 g), molecular sieve (5.0 g) and dichloromethane (50 mL), acetaldehyde (1.49 g) was added under nitrogen atmosphere at 3° C. Reaction mass was further cooled to −75° C. and added boron trifluoride etherate (6.16 g) below −65° C. and the reaction mass was stirred for 1 hour at −75° C. The temperature of the reaction mass was raised to ambient temperature and stirred for 60 minutes. The reaction mass was filtered to remove molecular sieve and the filtrate was washed with water (10 mL) followed by aqueous solution of saturated sodium bicarbonate (25 mL). The organic layer was concentrated completely and purified by column chromatography over silica gel using 7.5% ethyl acetate/n-hexane as eluant to afford the title compound.

Yield: 2.5 g

Example 6: Preparation of Methyl 3α-acetoxy-6-ethyl-7-keto-5β-cholanate (VI)

To a mixture of methyl 3α-acetoxy-6-ethylidene-7-keto-5β-cholanate (V) (15 g) and ethyl acetate (225 mL), palladium-charcoal (10%, 1.5 g) was added and the suspension was stirred under hydrogen pressure (45 psi) for 30-35 hours at 52° C. The reaction mass was filtered and the filter bed was washed with ethyl acetate (75 mL). The combined organic layer was concentrated under vacuum to afford the title compound.

Yield: 14.7 g

Example 7: Preparation of Methyl 3α-acetoxy-6α-ethyl-7-keto-5β-cholanate (VII)

To a mixture of methyl 3α-acetoxy-6-ethyl-7-keto-5β-cholanate (VI) (1.0 g) and toluene (5 mL) was added 1,8-diazabicyclo[5.4.0]undec-7-ene (0.80 g) and stirred the solution at reflux for 6 hours. The reaction mass was cooled to ambient temperature and washed with brine (10 mL). The aqueous layer was extracted with additional toluene (5 mL) and combined organic layer was washed with aqueous saturated sodium bicarbonate solution (10 mL). The organic layer was distilled completely under vacuum and chased with methanol (10 mL). The resulting residue was stirred in presence of methanol (2 mL) and filtered to obtain the title compound.

Yield: 0.425 g

Example 8: Preparation of Methyl 3α-hydroxy-6α-ethyl-7-keto-5β-cholanate (VIII)

To a mixture of methyl 3α-acetoxy-6α-ethyl-7-keto-5β-cholanate (VII) (11.5 g) in methanol (57.5 mL), concentrated sulfuric acid (1.15 mL) was added slowly at 30° C. The reaction mass was stirred at the same temperature for 1 hour and then at 45-50° C. for 2 hours. The reaction mass was cooled to 10° C. Saturated aqueous solution of sodium bicarbonate (34.5 mL) was added drop wise into the reaction mass. The reaction mass was concentrated up to 2 volumes under vacuum. The concentrated reaction mass was diluted with saturated aqueous solution of sodium bicarbonate (23 mL). The reaction mass was extracted with ethyl acetate (2×57.5 mL). The combined organic layer was distilled out under vacuum and chased with methanol (11.5 mL) to afford the desired product.

Yield: 10.5 g

Example 9: Preparation of Methyl 3α,7α-dihydroxy-6α-ethyl-5β-cholanate (IX)

A solution of methyl 3α-hydroxy-6α-ethyl-7-keto-5β-cholanate (VIII) (30 g) in methanol (75 mL) was cooled to 0-5° C. and sodium borohydride (0.53 g) was added in to the reaction mass under nitrogen atmosphere over a period of 5-10 minutes. The reaction mass was stirred at the same temperature for about 30 minutes. Another five lots of sodium borohydride (4×0.53 g) was added in to the reaction mass in the same manner. The reaction mass was stirred for 1-2 hours at about 0-5° C. The reaction was quenched by adding acetic acid (19.8 mL) slowly to the reaction mass below 5° C. The reaction mass was concentrated completely under vacuum below 50° C. till about 2-3 volumes of solvent remained. Ethyl acetate (150 mL) was added to the reaction mass and the reaction mass was washed with aqueous solution of sodium bicarbonate (28.8 g in 360 mL of water). The organic layer was separated. The aqueous layer was again extracted with ethyl acetate (150 mL) and the combined organic layer was washed with aqueous solution of sodium bicarbonate (7.5 g in 360 mL of water). The organic layer was completely concentrated under vacuum below 50° C. Methanol (75 mL) was added to the residue and heated to 40-50° C. for 20-30 minutes. The solution was cooled to 20-30° C. and the precipitated solid was filtered. The solid was washed with methanol (15 mL) to afford the desired compound.

Yield: 27.8 g
Purity (By HPLC): 94.57%

Example 10: Preparation of Obeticholic Acid (X)

To a mixture of methyl 3α,7α-dihydroxy-6α-ethyl-5β-cholanate (IX) (1 g) and methanol (5 mL), an aqueous solution of sodium hydroxide (18.4 mg in 2.75 mL of water) was added. The reaction mass was heated to 45-55° C. and stirred for 1-2 hours at 45-55° C. The reaction mass was distilled under vacuum to evaporate methanol below 50° C. Water (5 mL) was added to the residue and the reaction mass was acidified with phosphoric acid (0.25 mL) to pH 2-2.5. The aqueous layer was extracted with dichloromethane (2×10 mL). The combined organic layer was dried over sodium sulfate and evaporated to provide the crude desired compound. The crude compound was purified by column chromatography over silica gel using 60-80% ethyl acetate/n-hexane as eluant to provide the pure desired compound.

Yield: 0.82 g

Example 11: Preparation of Methyl 3α-acetoxy-7α-hydroxy-6α-ethyl-5β-cholanate (IXA)

To a mixture of methyl 3α-acetoxy-6α-ethyl-7-keto-5β-cholanate (VII) (0.5 g) in methanol (5 mL) and tetrahydrofuran (2.5 mL), sodium borohydride (40 mg) was added at about 0-5° C. and resulting reaction mixture was stirred for 2 hours at same temperature. Another lot of sodium borohydride (8 mg) was added to the reaction mass at the same temperature and the reaction mass was stirred for about 1 hour. The reaction mass was quenched with acetic acid (0.3 mL) and water (5 mL) and concentrated completely under vacuum. Saturated sodium bicarbonate solution (10 mL) was added to the residue and extracted with ethyl acetate (2×10 mL). Combined organic layer was concentrated completely under vacuum to afford the title compound.

Yield: 0.5 g

Example 12: Preparation of Obeticholic Acid (X)

An aqueous solution sodium hydroxide (0.714 g) in water (10.8 mL) was added to a solution of methyl 3α-acetoxy-7α-hydroxy-6α-ethyl-5β-cholanate (IXA) (4.0 g) in methanol (20 mL) at 25-30° C. The reaction mass was warmed to about 45-55° C. and maintained for 1-2 hours. The reaction mass was concentrated under vacuum and the residue was diluted with water (48 mL), washed with ethyl acetate (1×40 mL & 2×20 mL). The aqueous layer was acidified with dilute hydrochloric acid (6N) drop wise to a pH of about 1-2. The suspension was extracted with ethyl acetate (2×40 mL). The combined ethyl acetate layer was concentrated under vacuum to provide the desired product.

Yield: 3.75 g
Purity (By HPLC): 95.41%

Example 13: Preparation of Methyl 3α-trimethylsilyloxy-7-keto-5β-cholanate (IIIA)

To a solution of methyl 3α-hydroxy-7-keto-5β-cholanate (14.4 g) (II) in toluene (144 mL), triethylamine (7.2 g) was added under nitrogen atmosphere. Trimethyl silyl chloride (5.02 g) was added to the reaction mass at about 29° C. and stirred for 2 hours. The reaction mass was cooled to 5-10° C. and quenched with ice-cold water (144 mL). The organic layer was separated and the aqueous layer was extracted with toluene (43.2 mL). The combined organic layer was dried over sodium sulfate and concentrated up to about 5 volumes under vacuum to provide the title compound.

Example 14: Preparation of Methyl 3α, 7α-ditrimethylsilyloxy-5β-cholanate (IVA)

The solution of Example 13 was added to a mixture of sodium iodide (16.02 g), toluene (144 mL), acetonitrile (72 mL) and triethylamine (14.36 g). Trimethyl silyl chloride (11.57 g) was added to the reaction mass at about 25° C. and the reaction mass was stirred for 2 hours at about 45-55° C. The reaction mass was cooled to 10-20° C. and quenched with ice-cold water (144 mL). The organic layer was separated and the aqueous layer was extracted with toluene (72 mL). The combined organic layer was washed with water (72 mL), dried over sodium sulfate and evaporated under vacuum to provide the desired compound.

Yield: 20.1 g

Example 15: Preparation of Methyl 3α-hydroxy-6-ethylidene-7-keto-5β-cholanate (VA)

To a solution of methyl 3α, 7α-ditrimethylsilyloxy-5β-cholanate (IVA) (19 g) in dichloromethane (190 mL), boron trifluoride etherate (49.1 g) and acetaldehyde (6.09 g) was added at −60° C. The reaction mass was stirred for 1 hour at −60° C. and then at 1 hour at 25° C. The reaction mass was quenched by addition of saturated aqueous solution of sodium bicarbonate (285 mL) and the organic layer was separated. The aqueous layer was extracted with dichloromethane (95 mL). The combined organic layer was washed with water (95 mL), dried over sodium sulfate and evaporated under vacuum to provide the crude title compound, which was purified by column chromatography over silica gel using 25% ethyl acetate/n-hexane as eluant.

Yield: 8.50 g

Example 16: Preparation of Methyl 3α-acetoxy-6-ethylidene-7-keto-5β-cholanate (V)

To a solution of methyl 3α-hydroxy-6-ethylidene-7-keto-5β-cholanate (VA) (22.5 g) in dichloromethane (112.5 mL), triethylamine (13.22 g) and dimethyl amino pyridine (0.3 g) were added. The reaction mass was cooled to 0-5° C. and acetic anhydride (8 g) was added over a period of about 10 minutes. The reaction mass was allowed to warmed to 26-27° C. and stirred for 4 hours. The reaction mass was quenched with saturated aqueous solution of sodium bicarbonate (67.5 mL) and the organic layer was separated. The organic layer was washed with water (67.5 mL) and concentrated under vacuum to provide the crude title compound. The crude product was purified by column chromatography over silica gel using 7.5% ethyl acetate/n-hexane.

Yield: 17.2 g

Example 17: Preparation of Methyl 3α, 7α-ditrimethylsilyloxy-5β-cholanate (IVA)

A mixture of sodium iodide (250 g) and acetonitrile (300 mL) was stirred under nitrogen atmosphere at 27° C. for about 20 minutes. Toluene (600 mL) was added to the above reaction mass at the same temperature. The reaction mass was heated to reflux at 104° C. and solvent was distilled up to 1 volume. The reaction mass was then cooled to 71° C. and a second lot of toluene (750 mL) was added. The reaction mass was again heated to reflux at 108° C., maintained the reflux for 1 hour and the solvent was distilled up to 2 volumes. The reaction mass was cooled to 37° C. Acetonitrile (300 mL) was added to the above reaction mass at 37° C. and stirred for 30 minutes. The reaction mass was further cooled to 27° C. A solution of methyl 3α-hydroxy-7-keto-5β-cholanate (25 g) (II) in toluene (1500 mL) followed by acetonitrile (450 mL), triethylamine (206 g) and trimethylsilyl chloride (181 g) were added to the above reaction mass at 27° C. The reaction mass was heated to 51° C. and stirred for 2 hours. The reaction mass was then cooled to 26° C., toluene (750 mL) was added at the same temperature and further cooled to 15-16° C. A solution of sodium bicarbonate (75 g) and sodium thiosulphate pentahydrate (60 g) in water (1875 mL) was slowly added to the above reaction mass at 16° C., stirred for 15 minutes and then slowly warmed to 27° C. The organic layer was separated and aqueous layer was extracted with toluene (750 mL). The combined organic layers were washed with a solution of sodium bicarbonate (15 g) in water (450 mL) and concentrated under vacuum at 52° C. to afford the title compound.

Example 18: Preparation of Methyl 3α-hydroxy-6-ethylidene-7-keto-5β-cholanate (VA)

To a solution of methyl 3α, 7α-ditrimethylsilyloxy-5β-cholanate (IVA), as obtained in the example 17, in dichloromethane (1500 mL) was added molecular sieves (150 g) at 27° C. under nitrogen atmosphere and then cooled to 2-8° C. Acetaldehyde (57.2 g) was added to the above reaction mass at 3.7° C. and stirred for 30 minutes. The reaction mass was further cooled to −74.3° C. Boron trifluoride etherate (237 g) was slowly added to the above reaction mass at −74.3° C. for about 1 hour and the reaction mass was further stirred for 2 hours at the same temperature. The reaction mass was warmed to ambient temperature and stirred for 2 hours at the same temperature. The reaction mass was filtered to remove molecular sieve and washed with dichloromethane (450 mL). The filtrate was washed with water (1125 mL) and layers were separated. Organic layer was washed with an aqueous solution of sodium bicarbonate (1500 mL, 8% w/w) and layers were separated. Organic layer was again washed with an aqueous solution of sodium bicarbonate (750 mL, 4% w/w) and concentrated under vacuum at 45° C. The resulting residue was chased with ethyl acetate (300 mL) under vacuum at 49° C. (2 times) and the resulting crude was kept under vacuum at 55° C. for about 4-6 hours. Ethyl acetate (450 mL) was added to the above residue at 45° C. and stirred for 1 hour. The resulting reaction mass was then cooled to 31° C. and dried under vacuum to afford title compound.

Yield: 159.65 g

Example 19: Preparation of Methyl 3α-acetoxy-6-ethylidene-7-keto-5β-cholanate (V)

To a mixture of methyl 3α-hydroxy-6-ethylidene-7-keto-5β-cholanate (VA) (100 g) and ethyl acetate (200 mL), triethylamine (46.6 g) and dimethyl amino pyridine (2.82 g) were added. The reaction mass was cooled to 0-10° C. and acetic anhydride (35.3 g) was added over a period of about 10 minutes. The reaction mass was allowed to warm to 26-27° C. and stirred for 4 hours. The reaction mass was again cooled 5-10° C. and quenched with an aqueous solution of sodium bicarbonate (500 mL, 4% w/w). Organic layer was separated and aqueous layer was extracted with ethyl acetate (500 mL). Combined organic layers were washed with a solution of citric acid (500 mL, 10% w/w) and layers were separated. Organic layer was washed with a solution of sodium bicarbonate (500 mL, 4% w/w) to afford a solution of title compound in ethyl acetate.

Example 20: Preparation of Methyl 3α-acetoxy-6-ethyl-7-keto-5β-cholanate (VI)

To a solution of methyl 3α-acetoxy-6-ethylidene-7-keto-5β-cholanate (V) in ethyl acetate as obtained in the example 19 was added activated carbon (5 g) and stirred for 1 hour at 25-35° C. The reaction mass was filtered through hyflow and washed with ethyl acetate (200 mL). Palladium hydroxide (10%, 10 g) was added to the above filtrate and the suspension was stirred under hydrogen pressure (45 psi) for 8 hours at 52° C. The reaction mass was cooled to ambient temperature, added a second lot of palladium hydroxide (10%, 5 g) and the suspension was again stirred under hydrogen pressure (45 psi) for 8 hours at 52° C. The reaction mass was cooled to 27° C., held for 3 days at 25-35° C. in the absence of hydrogen gas. The reaction mass was filtered through hyflow and washed with ethyl acetate (200 L).

Filtrate was concentrated under vacuum to afford the title compound.

Example 21: Preparation of Methyl 3α-acetoxy-6α-ethyl-7-keto-5β-cholanate (VII)

To the residue as obtained in the example 20 was added toluene (200 mL) and distilled under vacuum at 45° C. A second lot of toluene (200 mL) was added to the above residue and distilled again under vacuum at 55° C. A third lot of toluene (500 mL) was added to the above residue and raised the temperature to 110-120° C. The reaction mass was refluxed at 112° C. to remove the water azeotropically. The reaction mass was then cooled to 70-80° C. and added 1,8-diazabicyclo[5.4.0]undec-7-ene (88 g) at the same temperature. The temperature of the reaction mixture was then raised to 110° C. and refluxed for about 16 hours. The reaction mass was cooled to ambient temperature and washed with brine (1000 mL, 20% w/w). The aqueous layer was extracted with toluene (500 mL) and combined organic layer was washed with aqueous sodium bicarbonate solution (1000 mL, 8% w/w).

The organic layer was washed with water (500 mL) and then distilled completely under vacuum at 50° C. Heptane (200 mL) was added to the above residue and distilled off completely under vacuum at 50° C. A second lot of heptane (200 mL) was added to the above residue and distilled off completely under vacuum at 50° C. To the resulting residue was added methanol (200 mL) and distilled off completely under vacuum at 50° C. A second lot of methanol (200 mL) was added to the above residue and distilled off completely under vacuum at 50° C. A third lot of methanol (125 mL) was added to the above residue at 30° C. and raised the temperature to 64° C. and reflux for 10 minutes. The temperature of the reaction mass was slowly cooled to 28° C. in a period of about 50 minutes. The temperature of the reaction mass was further cooled to 0-5° C. and stirred for 1 hour. Resulting solid was filtered and washed with chilled methanol (10 mL). The resulting residue was taken in methanol (225 mL) and refluxed at 62° C. for 30 minutes. The reaction mass was slowly cooled to −1.5° C. over a period of 2 hours. The solid was filtered and again washed with chilled methanol (75 mL), residue was taken in methanol (235 mL) and refluxed at 62° C. for 30 minutes. The reaction mass was slowly cooled to −1.7° C. over a period of 2 hours. The resulting solid was filtered and washed with chilled methanol (67 mL) and dried under vacuum at 50° C. to obtain the title compound.

Yield: 63.8 g

The invention claimed is:

1. A process for the preparation of obeticholic acid (X) comprising the steps of:

a) conversion of compound of formula (VI) to compound of formula (VII) using an organic base

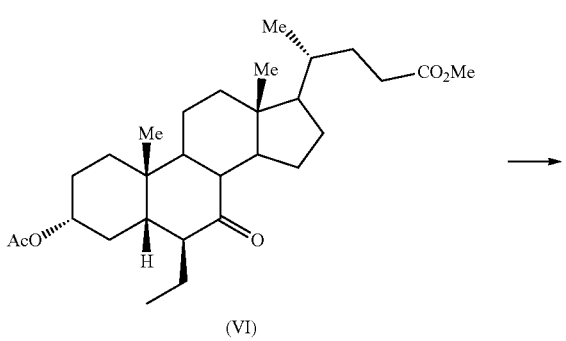

(VI)

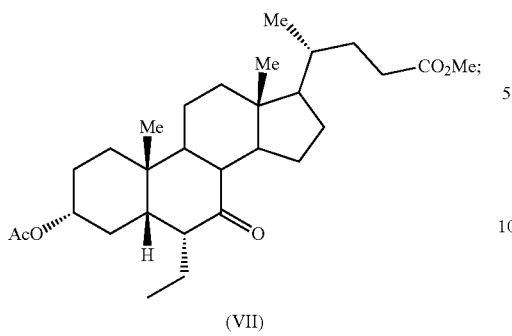

(VII)

b) reduction of compound of formula (VII) to provide compound of formula (IXA) in presence of sodium borohydride

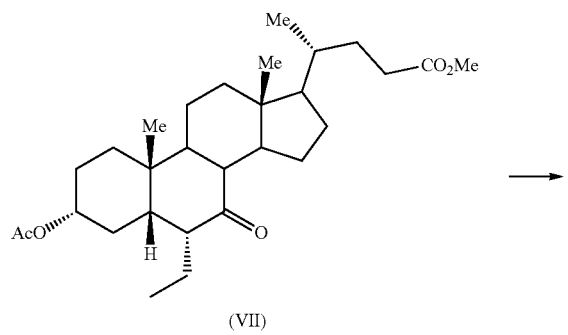

(VII)

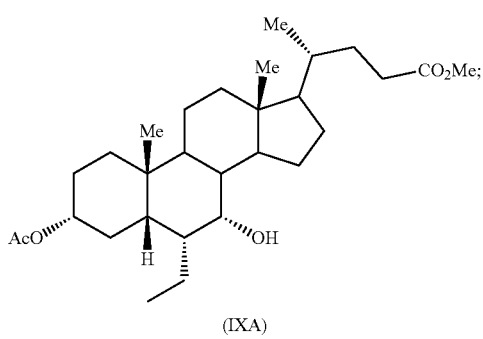

(IXA)

c) conversion of compound of formula (IXA) to obeticholic acid (X)

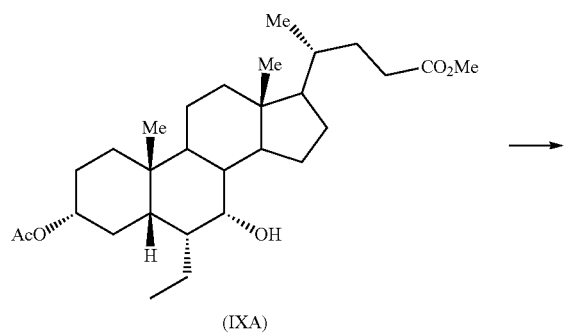

(IXA)

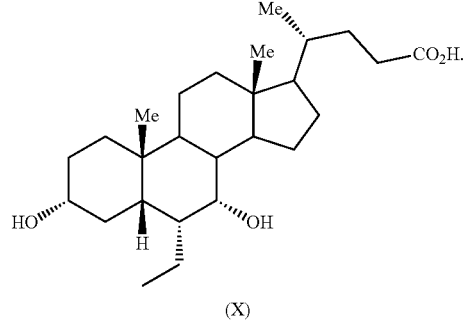

(X)

2. The process of claim 1, wherein the organic base in step a) is selected from a group of triethylamine, 1,4-diazabicyclo[2.2.2]octane, 1,8-diazabicyclo[5.4.0]undec-7-ene.

3. The process of claim 2, wherein the organic base in step a) is 1,8-diazabicyclo-[5.4.0]undec-7-ene.

4. The process of claim 1, wherein step (c) is carried out in presence of a base.

5. The process of claim 4, wherein the base is sodium hydroxide.

6. The process of claim 1, further comprising process for preparation of compound of formula (VI) comprising the steps of:

a) acetylation of compound of formula (VA) to provide compound of formula (V)

(VA)

(V)

b) hydrogenation of compound of formula (V) to provide compound of formula (VI)

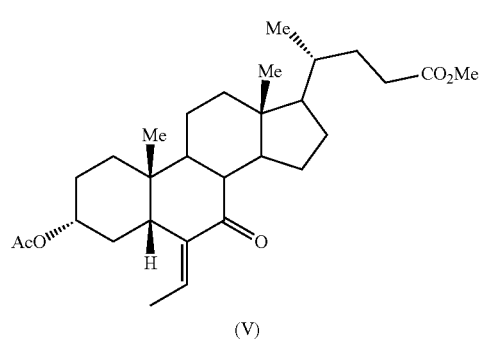

(V)

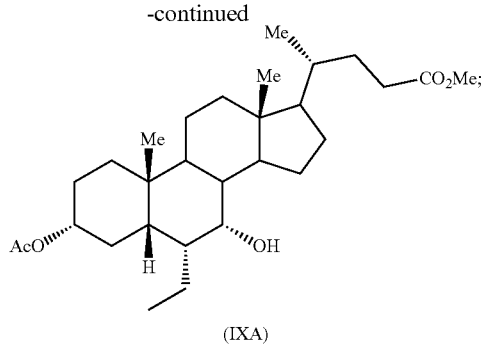

(IXA)

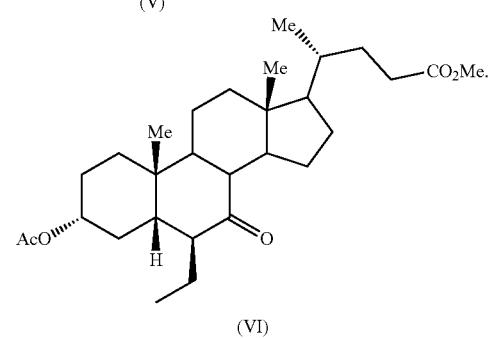

(VI)

b) conversion of compound of formula (IXA) to obeticholic acid (X)

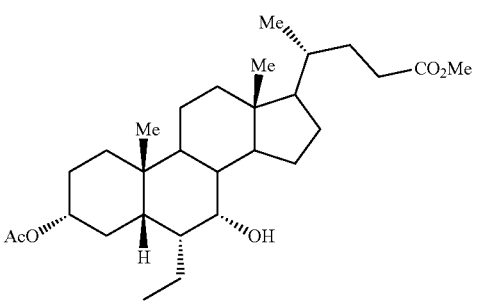

(IXA)

7. The process of claim 6, wherein acetylation in step (a) is carried out in presence of acetic anhydride.

8. A process for preparation of obeticholic acid (X) comprising steps of:
   a) reduction of compound of formula (VII) to provide compound of formula (IXA) in presence of sodium borohydride

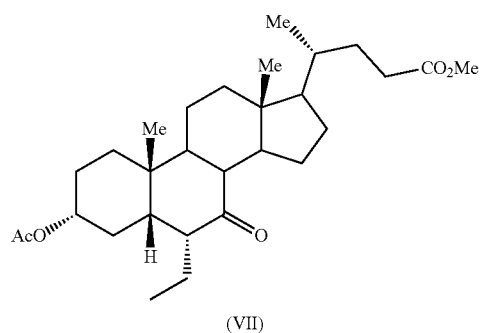

(VII)

(X)

9. The process of claim 8, wherein step (b) is carried out in presence of a base.

10. The process of claim 9, wherein the base is sodium hydroxide.

* * * * *